(12) United States Patent
Benning et al.

(10) Patent No.: US 6,642,436 B1
(45) Date of Patent: Nov. 4, 2003

(54) DNA ENCODING FOR PLANT DIGALACTOSYLDIACYLGLYCEROL GALACTOSYLTRANSFERASE AND METHODS OF USE

(75) Inventors: Christoph Benning, East Lansing, MI (US); Peter Döermann, Berlin (DE)

(73) Assignee: Board of Trustees operating Michigan State University, East Lansing, MI (US)

( * ) Notice: Subject to any disclaimer, the term of this patent is extended or adjusted under 35 U.S.C. 154(b) by 0 days.

(21) Appl. No.: 09/565,909

(22) Filed: May 5, 2000

Related U.S. Application Data

(60) Provisional application No. 60/132,849, filed on May 6, 1999.

(51) Int. Cl.$^7$ .......................... A01H 5/00; C12N 15/82
(52) U.S. Cl. .................... 800/281; 800/298; 435/252.3; 435/419; 435/468; 435/471; 435/320.1; 536/23.6
(58) Field of Search ............................ 536/23.2, 23.6; 435/69.1, 320.1, 468, 419, 471, 252.3; 800/278, 281, 298

(56) References Cited

PUBLICATIONS

De luca, "Molecular characterization of secondary metabolic pathways", 1993, AgBiotech News and Information vol. 5 No. 6, pp. 225n–229n.*

Van de Loo, "An oleate 12–hydroxylase from Ricinus communis L. is a fatty acyl desaturase homolog", Jul. 1995, Pro. Natl. Acad. Sci., vol. 92, pp. 6743–6747.*

Andersson, Lena et al., "Hydrolysis of galactolipids by human pancreatic lipolytic enzymes and duodenal contents," Journal Of Lipid Research, vol. 36, pp. 1392–1400 (1995).

Bechtold, Nicole et al., "In planta Agrobacterium mediated gene transfer by infiltrationof adult *Arabidopsis thaliana* plants," C. R. Acad. Sci. Paris Life Sci. 316, 1194–1199 (1993).

Becker, Detlef et al., "Binary vectors which allow the exchange of plant selectable markers and reporter genes," Nucleic Acids Research, vol. 18, No. 1, p. 203 (1990).

Bell, Callum J. et al., "Assignment of 30 Microsatellite Loci to the Linkage Map of Arabidopsis," Genomics 19, 137–144 (1994).

Bent, Andrew F. et al., "RPS2 of *Arabidopsis thaliana*: A Leucine–Rich Repeat Class of Plant Disease Resistance Genes," Science, vol. 265, 1856–1860, (1994).

Block, Maryse A. et al., "Preparation and Characterization of Membrane Fractions Enriched in Outer and Inner Envelope Membranes from Spinach Chloroplasts," The Journal of Biological Chemistry, vol. 258, No. 21, 13281–13286 (1983).

Browse, John et al., "Glycerolipids," Arabidopsis, E.M. Meyerowitz and C.R. Somerville, Eds. Lipids, 881–912 (1994).

Browse, John et al., "Glycerolipid Synthesis: Biochemistry and Regulation," Annu. Rev. Plant Physiol. Plant Mol. Biol. 42:467–506 (1991).

Browse, John et al., "Fluxes through the prokaryotic and eukaryotic pathways of lipid synthesis in the 16.3 plant *Arabidopsis thaliana*," Biochem J., vol. 235, pp. 25–31 (1986).

Camilleri, Christine et al., "A YAC contig map of *Arabidopsis thaliana* chromosome 3," The Plant Journal 14(5), 633–642 (1998).

Chang, Annie C. et al., "Construction and Characterization of Amplifiable Multicopy DNA Cloning Vehicles Derived from the P15A Cryptic Miniplasmid," Journal of Bacteriology, vol. 134, No. 3, pp. 1141–1156 (1978).

Cline, Kenneth et al., "Galactosyltransferases Involved in Galactolipid Biosynthesis Are Located in the Outer Membrane of Pea Chloroplast Envelopes," Plant Physiol. 71, 366–372 (1983).

Dörmann, Peter et al., "Isolation and Characterization of an Arabidopsis Mutant Deficient in the Thylakoid Lipid Digalactosyl Diacylglycerol," The Plant Cell, vol. 7, 1801–1810 (1995).

Dorne, Albert–Jean et al., "The galactolipid: galactolipid galactosyltransferase is located on the outer surface of the outer membrane of the chloroplast envelope," vol. 145, No. 1 (1992).

Härtel, Heiko, et al., "Photosynthetic light utilization and xanthophyll cycle activity in the galactolipid deficient dgd1 mutant of *Arabidopsis thaliana*,"Plant Physiol. Beichem, 36(6), 407–417 (1998).

Härtel, Heiko, et al., "Changes in the Composition of the Photosynthetic Apparatus in the Galactolipid–Deficient dgd1 Mutant of *Arabidopsis thaliana*," Plant Physiol., 115: 1175–1184 (1997).

Heinz, Ernest et al., "Similarities and Differences in Lipid Metabolism of Chloroplasts Isolated from 18:3 and 16:3 Plants," Plant Physiol. 72, 273–279 (1983).

Heemskerk, Johan W.M. et al., Biosynthesis of Digalactosyldiacylglycerol in Plastids from 16:3 and 18:3 Plants, Plant Physiol. 93, 1286–1294 (1990).

(List continued on next page.)

Primary Examiner—Elizabeth F. McElwain
(74) Attorney, Agent, or Firm—Harness, Dickey & Pierce, P.L.C.

(57) ABSTRACT

The cDNA encoding digalactosyldiacylglycerol galactosyltransferase (DGD1) is provided. The deduced amino acid sequence is also provided. Methods of making and using DGD1 to screen for new herbicides and alter a plant's leaf lipid composition are also provided, as well as expression vectors, transgenic plants or other organisms transfected with said vectors.

19 Claims, 4 Drawing Sheets

OTHER PUBLICATIONS

Joyard, Jacques et al.,"The Biochemical Machinery of Plastid Envelope Membranes," Plant Physiol. 118: 715–723 (1998).

Kunst, Ljerka et al., "Altered regulation of Lipid biosynthesis in a mutant of Arabidopsis deficient in chloroplast glycerol–3–phosphate acyltransferase activity," Proc. Natl. Acad. Sci USA, vol. 85, pp. 4143–4147 (1988).

Chen, Lih–Jen et al., "A Mutant deficient in the plastid lipid DGD is defective in protein import into chloroplasts," The Plant Journal, 16(1), 33–39 (1998).

Maréchal, Eric et al., "Kinetic Properties of Monogalactosyldiacylglycerol Synthase from Spinach Chloroplast Envelope Membranes," The Journal of Biological Chemistry, vol. 269, No. 8, pp. 5788–5798 (1994).

Meyer, Knut et al., "Cloning of Plant Genes based on the Genetic Map Position," Genome Mapping in Plants, A.H. Patterson, Ed. pp. 137–154, Academic Press, New York (1996).

Mongrand, Sébastien et al., "The $C_{16:3}/C_{18:3}$ Fatty Acid Balance In Photosynthetic Tissues From 468 Plant Species," Phytochemistry, vol. 49, No. 4, pp. 1049–1064 (1998).

Mozo, T. et al., "Construction and characterization of the IGF Arabidopsis BAC library," Mol Gen Genet 258: 562–570 (1998).

Ohlsson, Lena et al., "Orally Fed Digalactosyldiacylglycerol Is Degraded during Absorption in Intact and Lymphatic Duct Cannulated Rats," Nutrient Metabolism, pp. 239–245 (1998).

Reifarth, F. et al., "Modification of the Water Oxidizing Complex in Leaves of the dgd1 Mutant of *Arabidopsis thaliana*, Deficient in the Galactolipid Digalactosyldiacyglycerol," Biochemistry, 36, 11769–11776 (1997).

Shimojima, Mie et al., "Cloning of the gene for monogalactosyldiacylglycerol synthase and its evolutionary origin," Proc. Natl. Acad. Sci. USA, vol. 94, pp. 333–337 (1997).

Teucher, T. et al., "Purification of UDP–galactose: diacylglycerol galactosyltransferase from chloroplast envelopes of spinach (*Spinacia oleracea* L.)," Planta, 184: 319–326 (1991).

Uwer, Ursula et al., "Inactivation of a Glycyl–tRNA Synthetase Leads to an Arrest in Plant Embryo Development," The Plant Cell, vol. 10, 1277–1294 (1998).

Van Besouw, Aernout et al., "Galactolipid Formation in Chloroplast Envelopes," Biochimica et Biophysica Acts, 529, 44–53 (1978).

Office action for Canadian Application No. 2,307,960 entitled "DNA Encoding for Plant Digalactosyldiacylglycerol Galactosyltransferase and Methods of Use" dated Nov. 6, 2002 received by Canadian Associate on Nov. 12, 2002.

Marechal et al., *Lipis synthesis and metabolism in the plastid envelope*, Physiologia Plantarum 1997, 100: pp. 65–77.

Genbank DNA sequence Accession #AC009918, Sep. 8, 1999: Lin et al.

Genbank DNA sequence Accession #AF058919, Apr. 15, 1998: Geisel, C.

* cited by examiner

SEQUENCE LISTING

<160> NUMBER OF SEQ ID NOS: 8

<210> SEQ ID NO 1
<211> LENGTH: 2649
<212> TYPE: DNA
<213> ORGANISM: Arabidopsis thaliana

<400> SEQUENCE: 1

-continued

| | |
|---|---|
| gaattcggca cgaggcagca ctctcacgaa atcgtcgtga cgaaacgata aaccctaagt | 60 |
| catggtaaag gaaactctaa ttcctccgtc atctacgtca atgacgaccg gaacatcttc | 120 |
| ttcttcgtct cttttcaatga cgttatcctc aacaaacgcg ttatcgtttt tgtcgaaagg | 180 |
| atggagagag gtatgggatt cagcagatgc ggatttgcag ctgatgcgag acagagctaa | 240 |
| ctctgttaag aatctagcat caacgttcga tagagagatc gagaatttcc tcaataactc | 300 |
| ggcgaggtct gcgtttcccg ttggttcacc atcggcgtcg tctttctcaa atgaaattgg | 360 |
| tatcatgaag aagcttcagc cgaagatttc ggagtttcgt agggtttatt cggcgccgga | 420 |
| gattagtcgc aaggttatgg agagatgggg acctgcgaga gcgaagcttg gaatggatct | 480 |
| atcggcgatt aagaaggcga ttgtgtctga gatggaattg gatgagcgtc agggagtttt | 540 |
| ggagatgagt agattgagga gacggcgtaa tagtgatagg gttaggttta cggagttttt | 600 |
| cgcggaggct gagagagatg gagaagctta tttcggtgat tgggaaccga ttaggtcttt | 660 |
| gaagagtaga tttaaagagt ttgagaaacg aagctcgtta gaaatattga gtggattcaa | 720 |
| gaacagtgaa tttgttgaga agctcaaaac cagcttaaa tcaatttaca agaaactga | 780 |
| tgaggctaag gatgtccctc cgttggatgt acctgaactg ttggcatgtt tggttagaca | 840 |
| atctgaacct tttcttgatc agattggtgt tagaaaggat acatgtgacc gaatagtaga | 900 |
| aagcctttgc aaatgcaaga gccaacaact ttggcgtctg ccatctgcac aagcatccga | 960 |
| tttaattgaa aatgataacc atggagttga tttggatatg aggatagcca gtgttcttca | 1020 |
| aagcacagga caccattatg atggtgggtt ttggactgat tttgtgaagc ctgagacacc | 1080 |
| ggaaaacaaa aggcatgtgg caattgttac aacagctagt cttccttgga tgaccggaac | 1140 |
| agctgtaaat ccgctattca gagcggcgta tttggcaaaa gctgcaaaac agagtgttac | 1200 |
| tctcgtggtt ccttggctct gcgaatctga tcaagaacta gtgtatccaa acaatctcac | 1260 |
| cttcagctca cctgaagaac aagagagtta tatacgtaaa tggttggagg aaaggattgg | 1320 |
| tttcaaggct gattttaaaa tctccttta cccaggaaag ttttcaaaag aaaggcgcag | 1380 |
| catatttcct gctggtgaca cttctcaatt tatatcgtca aaagatgctg acattgctat | 1440 |
| acttgaagaa cctgaacatc tcaactggta ttatcacggc aagcgttgga ctgataaatt | 1500 |
| caaccatgtt gttggaattg tccacacaaa ctacttagag tacatcaaga gggagaagaa | 1560 |
| tggagctctt caagcatttt ttgtgaacca tgtaaacaat tgggtcacac gagcgtattg | 1620 |
| tgacaaggtt cttcgcctct ctgcggcaac acaagattta ccaaagtctg ttgtatgcaa | 1680 |
| tgtccatggt gtcaatccca agttccttat gattggggag aaaattgctg aagagagatc | 1740 |
| ccgtggtgaa caagctttct caaaaggtgc atacttctta ggaaaaatgg tgtgggctaa | 1800 |
| aggatacaga gaactaatag atctgatggc taaacacaaa agcgaacttg ggagcttcaa | 1860 |
| tctagatgta tatgggaacg gtgaagatgc agtcgaggtc caacgtgcag caaagaaaca | 1920 |
| tgacttgaat ctcaatttcc tcaaaggaag ggaccacgct gacgatgctc ttcacaagta | 1980 |
| caaagtgttc ataaacccca gcatcagcga tgttctatgc acagcaaccg cagaagcact | 2040 |
| agccatgggg aagtttgtgg tgtgtgcaga tcacccttca aacgaattct ttagatcatt | 2100 |
| cccgaactgc ttaacttaca aaacatccga agactttgtg tccaaagtgc aagaagcaat | 2160 |
| gacgaaagag ccactacctc tcactcctga acaaatgtac aatctctctt gggaagcagc | 2220 |
| aacacagagg ttcatggagt attcagatct cgataagatc ttaaacaatg agagggagg | 2280 |
| aaggaagatg cgaaaatcaa gatcggttcc gagctttaac gaggtggtcg atggaggatt | 2340 |

```
ggcattctca cactatgttc taacagggaa cgatttcttg agactatgca ctggagcaac    2400
accaagaaca aaagactatg ataatcaaca ttgcaaggat ctgaatctcg taccacctca    2460
cgttcacaag ccaatcttcg ctggtagat  atttccccat aggccaccca gttattgctt    2520
gtgacttatt aaaccactac gttattgtta tccttttta  cttttacagt tgttgtaggt    2580
cgtttgtttg ttaatagaaa gggtagatta ttattaaaaa aaaaaaaaa  aaaaaaaaa     2640 aaactcgag                                                            2649

<210> SEQ ID NO 2
<211> LENGTH: 808
<212> TYPE: PRT
<213> ORGANISM: Arabidopsis thaliana

<400> SEQUENCE: 2

Met Val Lys Glu Thr Leu Ile Pro Pro Ser Thr Ser Met Thr Thr
 1               5                  10                  15

Gly Thr Ser Ser Ser Ser Leu Ser Met Thr Leu Ser Ser Thr Asn
                20                  25                  30

Ala Leu Ser Phe Leu Ser Lys Gly Trp Arg Glu Val Trp Asp Ser Ala
                35                  40                  45

Asp Ala Asp Leu Gln Leu Met Arg Asp Arg Ala Asn Ser Val Lys Asn
        50                  55                  60

Leu Ala Ser Thr Phe Asp Arg Glu Ile Glu Asn Phe Leu Asn Asn Ser
 65                 70                  75                  80

Ala Arg Ser Ala Phe Pro Val Gly Ser Pro Ser Ala Ser Ser Phe Ser
                85                  90                  95

Asn Glu Ile Gly Ile Met Lys Lys Leu Gln Pro Lys Ile Ser Glu Phe
            100                 105                 110

Arg Arg Val Tyr Ser Ala Pro Glu Ile Ser Arg Lys Val Met Glu Arg
        115                 120                 125

Trp Gly Pro Ala Arg Ala Lys Leu Gly Met Asp Leu Ser Ala Ile Lys
    130                 135                 140

Lys Ala Ile Val Ser Glu Met Glu Leu Asp Arg Gln Gly Val Leu
145                 150                 155                 160

Glu Met Ser Arg Leu Arg Arg Arg Asn Ser Asp Arg Val Arg Phe
                165                 170                 175

Thr Glu Phe Phe Ala Glu Ala Glu Arg Asp Gly Glu Ala Tyr Phe Gly
            180                 185                 190

Asp Trp Glu Pro Ile Arg Ser Leu Lys Ser Arg Phe Lys Glu Phe Glu
        195                 200                 205

Lys Arg Ser Ser Leu Glu Ile Leu Ser Gly Phe Lys Asn Ser Glu Phe
    210                 215                 220

Val Glu Lys Leu Lys Thr Ser Phe Lys Ser Ile Tyr Lys Glu Thr Asp
225                 230                 235                 240

Glu Ala Lys Asp Val Pro Pro Leu Asp Val Pro Glu Leu Leu Ala Cys
                245                 250                 255

Leu Val Arg Gln Ser Glu Pro Phe Leu Asp Gln Ile Gly Val Arg Lys
            260                 265                 270

Asp Thr Cys Asp Arg Ile Val Glu Ser Leu Cys Lys Cys Lys Ser Gln
        275                 280                 285

Gln Leu Trp Arg Leu Pro Ser Ala Gln Ala Ser Asp Leu Ile Glu Asn
    290                 295                 300

Asp Asn His Gly Val Asp Leu Asp Met Arg Ile Ala Ser Val Leu Gln
305                 310                 315                 320
```

-continued

```
Ser Thr Gly His His Tyr Asp Gly Gly Phe Trp Thr Asp Phe Val Lys
            325                 330                 335

Pro Glu Thr Pro Glu Asn Lys Arg His Val Ala Ile Val Thr Thr Ala
            340                 345                 350

Ser Leu Pro Trp Met Thr Gly Thr Ala Val Asn Pro Leu Phe Arg Ala
            355                 360                 365

Ala Tyr Leu Ala Lys Ala Ala Lys Gln Ser Val Thr Leu Val Val Pro
370                 375                 380

Trp Leu Cys Glu Ser Asp Gln Glu Leu Val Tyr Pro Asn Asn Leu Thr
385                 390                 395                 400

Phe Ser Ser Pro Glu Glu Gln Glu Ser Tyr Ile Arg Lys Trp Leu Glu
            405                 410                 415

Glu Arg Ile Gly Phe Lys Ala Asp Lys Ile Ser Phe Tyr Pro Gly
            420                 425                 430

Lys Phe Ser Lys Glu Arg Arg Ser Ile Phe Pro Ala Gly Asp Thr Ser
            435                 440                 445

Gln Phe Ile Ser Ser Lys Asp Ala Asp Ile Ala Ile Leu Glu Glu Pro
            450                 455                 460

Glu His Leu Asn Trp Tyr Tyr His Gly Lys Arg Trp Thr Asp Lys Phe
465                 470                 475                 480

Asn His Val Val Gly Ile Val His Thr Asn Tyr Leu Glu Tyr Ile Lys
            485                 490                 495

Arg Glu Lys Asn Gly Ala Leu Gln Ala Phe Val Asn His Val Asn
            500                 505                 510

Asn Trp Val Thr Arg Ala Tyr Cys Asp Lys Val Leu Arg Leu Ser Ala
            515                 520                 525

Ala Thr Gln Asp Leu Pro Lys Ser Val Val Cys Asn Val His Gly Val
            530                 535                 540

Asn Pro Lys Phe Leu Met Ile Gly Glu Lys Ile Ala Glu Glu Arg Ser
545                 550                 555                 560

Arg Gly Glu Gln Ala Phe Ser Lys Gly Ala Tyr Phe Leu Gly Lys Met
            565                 570                 575

Val Trp Ala Lys Gly Tyr Arg Glu Leu Ile Asp Leu Met Ala Lys His
            580                 585                 590

Lys Ser Glu Leu Gly Ser Phe Asn Leu Asp Val Tyr Gly Asn Gly Glu
            595                 600                 605

Asp Ala Val Glu Val Gln Arg Ala Ala Lys Lys His Asp Leu Asn Leu
            610                 615                 620

Asn Phe Leu Lys Gly Arg Asp His Ala Asp Ala Leu His Lys Tyr
625                 630                 635                 640

Lys Val Phe Ile Asn Pro Ser Ile Ser Asp Val Leu Cys Thr Ala Thr
            645                 650                 655

Ala Glu Ala Leu Ala Met Gly Lys Phe Val Val Cys Ala Asp His Pro
            660                 665                 670

Ser Asn Glu Phe Phe Arg Ser Phe Pro Asn Cys Leu Thr Tyr Lys Thr
            675                 680                 685

Ser Glu Asp Phe Val Ser Lys Val Gln Glu Ala Met Thr Lys Glu Pro
            690                 695                 700

Leu Pro Leu Thr Pro Glu Gln Met Tyr Asn Leu Ser Trp Glu Ala Ala
705                 710                 715                 720

Thr Gln Arg Phe Met Glu Tyr Ser Asp Leu Asp Lys Ile Leu Asn Asn
            725                 730                 735

Gly Glu Gly Gly Arg Lys Met Arg Lys Ser Arg Ser Val Pro Ser Phe
```

```
                    740             745             750
Asn Glu Val Val Asp Gly Gly Leu Ala Phe Ser His Tyr Val Leu Thr
            755             760             765
Gly Asn Asp Phe Leu Arg Leu Cys Thr Gly Ala Thr Pro Arg Thr Lys
    770             775             780
Asp Tyr Asp Asn Gln His Cys Lys Asp Leu Asn Leu Val Pro Pro His
785             790             795             800
Val His Lys Pro Ile Phe Gly Trp
                805

<210> SEQ ID NO 3
<211> LENGTH: 2500
<212> TYPE: DNA
<213> ORGANISM: Arabidopsis thaliana
<220> FEATURE:
<221> NAME/KEY: misc_feature
<222> LOCATION: (467)..(983)
<223> OTHER INFORMATION: exon 1
<221> NAME/KEY: misc_feature
<222> LOCATION: (1201)..(1427)
<223> OTHER INFORMATION: exon 2
<221> NAME/KEY: misc_feature
<222> LOCATION: (1608)..(1874)
<223> OTHER INFORMATION: exon 3
<221> NAME/KEY: misc_feature
<222> LOCATION: (1987)..(2073)
<223> OTHER INFORMATION: exon 4
<221> NAME/KEY: misc_feature
<222> LOCATION: (2261)..(2332)
<223> OTHER INFORMATION: exon 5

<400> SEQUENCE: 3
tgtgggatta agattctata ttatctttt gataataaaa acaaaaatat tagcaaaata      60
gaaaagattc acaagatctt tattagaaga aaagtgaatg gtatgcataa ataaaatcca    120
tgaaaagtaa accattaatg cacaggacac gagttactca tagttcatat gttaaatggt    180
tttcttatta gcaattagat atggctctaa tatgagcaat tggccacata agtggacaaa    240
tgcgaattcg aaatgatatg tacagcttct gattctttta atggaatcat atactaaatt    300
ttataattca gactcgtgtc atcatacatg ttccacaaga tgaaaaatct aactttcatc    360
atcaatatta caccaaagct gctatagaat gattcagata gtatacattg atttatacac    420
aaaaatatcc caatgatatg cagacaaaga taaattaaaa aacaggtcaa tcttgcttgc    480
gagtatttgg ggaaggagtg ttgagagaca accaagatc tctacataac tcttcatcgg     540
gctgcaagct tccaggtata gcaccaaaag ctgttctgga agcttcaaat ccagacgcca    600
agaaatgaat atacgctgac atatcctcca agtttttccc cacactaatc gaagatgacg    660
caaacacact tctctttgac aagttcgaat cagctcttga taaccggttc agatcagaga    720
ctttttataaa ccgttgtgta gcagcttccc atgatagttc atgcctttgt tgctctgtaa    780
gttgcgatgg ttgttcccca agagccttga gcgtggctct tacaaaacct tgtccatcgt    840
cataggttct gcagttggga aactgtttga agaacttgtt cgatatgtga ttcgcgcata    900
ctactatttt tcccatcgcc aaggcttctg cagttgttgt acacacaacg tctgtcgtgc    960
tggggttgag aaacactta tagctgaaaa tagaagatgg aaaagtttaa ggtatagaat     1020
ccgatagact gcaaggaaat caatcaatct tgaggctgtt aagaactaga gacttacttg    1080
tgaaatagcg agtcagcgtg atcacgtcct gggtaaacat taaccgtcaa gtcgagtttt    1140
cgggctgctt ctttgatctc ttcagagtcc tctccatcac cgtataaatc aacctctaac    1200
tcggcaagtt ccttttggtg tttctcaagt agtttaagaa gctccttgta cccctttgctc   1260
```

```
cagaccatct taccaatgta gtatgcgcct ttagtgaagg gctgctcctg gagcttctgc   1320
tgttctagtt ttctcaaccc aatttcgaga aatttagggt tgacgccatg aacattgcag   1380
actatagatt tagggtattc ttgagtcgca gcagataacc tgattacctg caggagtaac   1440
atcattggta caagtcctga ttcacatcaa aaggaccggc cataattgtg gtcacattcc   1500
aacaaactgt cttgattctc aaattaaacc cagccattgg atatattcac ataattgagc   1560
aatcactcta tcatgtccta gtggctgtaa agaagaaaga agtttacctt gtggcagtaa   1620
atgccaacaa cccaactatt taagtatttg aggaaaaatg ctttgacacg gccttgtttc   1680
tctcttttaa cgtattccaa gtagttagtg tgtacgattc ctatgacgta gttgaactta   1740
gttttccatt tttggccatg atgaaaccat gtgagatgct caggctcctc gaggacagca   1800
atgtctgcct cttcatcagg aatggcatca gatatatccc caacaggaag aatactcctt   1860
ttgtcaatag caaactgcca taagataaat ttgaattgct aaggttggca caacacagtc   1920
acagagtact acgtaaaaga aatggaagaa ttcaactcta tatcacacgg aaatgaaaca   1980
atcgactcta tgaaaggaag cagtatgtgt ttggtaccca aaagaagatt cttgagagtc   2040 ataccttttcc aggatagaaa cgtatctcaa aggctaaacg aaaagagact ctctcctcaa   2100
gccactggcg gacataagct tcttgctctg acggggaact aaaagtgatg ctatttgggt   2160
agacaagctt ttggtgcttc aaagtcagcc atggaatcac caacgtgacc cgtctttccc   2220
catcatttgc aagtaggca gcacggaaga gaggattaac agcagttccc gtaagccatg   2280
gaatactagc tgttgtaaat atcgcaatgt gttgctcctg ctgattagtc atatcatctc   2340
aagctaaacc tctacaaatt atcaaacaaa aagagtaaac caatagattc ttgtaattga   2400
gtttgatctg attattgcat cttcccaata aggataacat tcgactacaa attcttaatt   2460
tttctgcaaa ttcaaacaat cttttcacac gattcaagcg                        2500

<210> SEQ ID NO 4
<211> LENGTH: 389
<212> TYPE: PRT
<213> ORGANISM: Arabidopsis thaliana

<400> SEQUENCE: 4

Met Thr Asn Gln Gln Glu Gln His Ile Ala Ile Phe Thr Thr Ala Ser
 1               5                  10                  15

Ile Pro Trp Leu Thr Gly Thr Ala Pro Leu Arg Tyr Val Ser Ile Leu
             20                  25                  30

Glu Arg Tyr Asp Ser Gln Glu Ser Ser Phe Gly Tyr Gln Thr His Thr
         35                  40                  45

Ala Ser Phe His Arg Phe Ala Ile Asp Lys Arg Ser Ile Leu Pro Val
     50                  55                  60

Gly Asp Ile Ser Asp Ala Ile Pro Asp Glu Glu Ala Asp Ile Ala Val
 65                  70                  75                  80

Leu Glu Glu Pro Glu His Leu Thr Trp Phe His Gly Gln Lys Trp
                 85                  90                  95

Lys Thr Lys Phe Asn Tyr Val Ile Gly Ile Val His Thr Asn Tyr Leu
            100                 105                 110

Glu Tyr Val Lys Arg Glu Lys Gln Gly Arg Val Lys Ala Phe Phe Leu
        115                 120                 125

Lys Tyr Leu Asn Ser Trp Val Val Gly Ile Tyr Cys His Lys Val Ile
    130                 135                 140

Arg Leu Ser Ala Ala Thr Gln Glu Tyr Pro Lys Ser Ile Val Cys Asn
```

-continued

```
                145                 150                 155                 160
Val His Gly Val Asn Pro Lys Phe Leu Glu Ile Gly Leu Arg Lys Leu
                    165                 170                 175
Glu Gln Gln Lys Leu Gln Glu Gln Pro Phe Thr Lys Gly Ala Tyr Tyr
                180                 185                 190
Ile Gly Lys Met Val Trp Ser Lys Gly Tyr Lys Glu Leu Leu Lys Leu
                195                 200                 205
Leu Glu Lys His Gln Lys Glu Leu Ala Asp Tyr Lys Val Phe Leu Asn
            210                 215                 220
Pro Ser Thr Thr Asp Val Val Cys Thr Thr Ala Glu Ala Leu Ala
225                 230                 235                 240
Met Gly Lys Ile Val Val Cys Ala Asn His Ile Ser Asn Lys Phe Phe
                245                 250                 255
Lys Gln Phe Pro Asn Cys Arg Thr Tyr Asp Asp Gly Gln Gly Phe Val
                260                 265                 270
Arg Ala Thr Leu Lys Ala Leu Gly Glu Gln Pro Ser Gln Leu Thr Glu
                275                 280                 285
Gln Gln Arg His Glu Leu Ser Trp Glu Ala Ala Thr Gln Arg Phe Ile
            290                 295                 300
Lys Val Ser Asp Leu Asn Arg Leu Ser Arg Ala Asp Ser Asn Leu Ser
305                 310                 315                 320
Lys Arg Ser Val Phe Ala Ser Ser Ile Ser Val Gly Lys Asn Leu
                325                 330                 335
Glu Asp Met Ser Ala Tyr Ile His Phe Leu Ala Ser Gly Phe Glu Ala
                340                 345                 350
Ser Arg Thr Ala Phe Gly Ala Ile Pro Gly Ser Leu Gln Pro Asp Glu
                355                 360                 365
Glu Leu Cys Arg Asp Leu Gly Leu Ser Leu Asn Thr Pro Ser Pro Asn
            370                 375                 380
Thr Arg Lys Gln Asp
385

<210> SEQ ID NO 5
<211> LENGTH: 5128
<212> TYPE: DNA
<213> ORGANISM: Arabidopsis thaliana
<220> FEATURE:
<221> NAME/KEY: misc_feature
<222> LOCATION: (627)..(1369)
<223> OTHER INFORMATION: exon 1
<221> NAME/KEY: misc_feature
<222> LOCATION: (1565)..(1597)
<223> OTHER INFORMATION: exon 2
<221> NAME/KEY: misc_feature
<222> LOCATION: (1712)..(1798)
<223> OTHER INFORMATION: exon 3
<221> NAME/KEY: misc_feature
<222> LOCATION: (2186)..(2668)
<223> OTHER INFORMATION: exon 4
<221> NAME/KEY: misc_feature
<222> LOCATION: (2769)..(3035)
<223> OTHER INFORMATION: exon 5
<221> NAME/KEY: misc_feature
<222> LOCATION: (3137)..(3487)
<223> OTHER INFORMATION: exon 6
<221> NAME/KEY: misc_feature
<222> LOCATION: (3570)..(4207)
<223> OTHER INFORMATION: exon 7
<221> NAME/KEY: gene
<222> LOCATION: (674)..(4079)
<223> OTHER INFORMATION: coding region for DGD1

<400> SEQUENCE: 5
```

```
aagctttaac gagagcgatc aaaggcaaat cactagaaac tcttgagcaa gagttcatgt    60
cgaccgtgat attttgtatg atatatatat ggtcaagatg gtgaagacaa aggttctact   120
attgtataat ggtatcaaaa tttgctaaat ttctaacaat ttcacaaggt ctcgcgtggc   180
gtccgttggt tgtttggtt aagtcggcct ctattttgat ccgttaatgg aactcgttac    240
ggtctaatta cgtccactga tatcactttc caatgttttt ttttgttaaa tgtcattgtc   300
aataccatgc cccgtaggac cagattcttc gattccagca tattcctaag ttaaatccga   360
cacaatcgga taatctcgtc aaccactcac aacacgccac gtaatcaatg atgtggaacc   420
catgccacgt tggacacggt ctcacgggac aaggcttcag taaagagcgc ctatcgtccg   480
tccgacttgt ttattttcca cgtgttaatc ttccagaata atcagaaaga gaattaaaaa   540
aataaaacaa tccaaattaa tctcagccgt caatttctct tcttcttctt cccaaattct   600
ctcaacagat agagaaaacc ttattagcag cactctcacg aaatcgtcgt gacgaaacga   660
taaaccctaa gtcatggtaa aggaaactct aattcctccg tcatctacgt caatgacgac   720
cggaacatct tcttcttcgt ctctttcaat gacgttatcc tcaacaaacg cgttatcgtt   780
tttgtcgaaa ggatggagag aggtatggga ttcagcagat gcggatttgc agctgatgcg   840
agacagagct aactctgtta agaatctagc atcaacgttc gatagagaga tcgagaattt   900
cctcaataac tcggcgaggt ctgcgtttcc cgttggttca ccatcggcgt cgtctttctc   960
aaatgaaatt ggtatcatga agaagcttca gccgaagatt tcggagtttc gtagggttta  1020
ttcggcgccg gagattagtc gcaaggttat ggagagatgg ggacctgcga gagcgaagct  1080
tggaatggat ctatcggcga ttaagaaggc gattgtgtct gagatggaat tggatgagcg  1140
tcagggagtt ttggagatga gtagattgag gagacggcgt aatagtgata gggttaggtt  1200
tacggagttt ttcgcggagg ctgagagaga tggagaagct tatttcggtg attgggaacc  1260
gattaggtct ttgaagagta gatttaaaga gtttgagaaa cgaagctcgt tagaaatatt  1320
gagtggattc aagaacagtg aatttgttga gaagctcaaa accagctttg taagtttctc  1380
caactttttg ggaacctatt tcaaaagttt cttctatctt actgtagaag tggcttctct  1440
ttcaatagcc acgacatttt cgtatgctga cttgatagtt actgttcttg gaatgattga  1500
ttgagtttct tatggtgttt ggcaactttt ctaatggtgc tttttttcttt tgttttattt  1560
gcagaaatca atttacaaag aaactgatga ggctaaggtt ggtatttgga agttggagct  1620
ctatcagttt ttccttgttac tttatatatt tttaggtcga gttcagtgtt ggattgggag  1680
tttaacttgg cctcctttta ctttggtgca ggatgtccct ccgttggatg tacctgaact  1740
gttggcatgt ttggttagac aatctgaacc ttttcttgat cagattggtg ttagaaaggg  1800
taagattgca tttttctctt catgatggtt aattattttg tctgttgtat gtattgagtt  1860
gtttctctac cataggtggt ttttccgtca aagtttgaa tcttctctct gatattagag   1920
tgtctttgtt aagtgggttg cttgcttcac cagaagttta gatggtgaga tttgatgttc  1980
tgcattatca cactaatcct ggatatcaaa tatgtgtaag tctagattct gtatgagaca  2040
gatcaatcaa atgacatctg ccgtagacat aaaaatttct agatgtgtag gttattggtt  2100
ttaaacaccc ttttcttgtac attatcttat agtttcagtg tttacataca aagttcctga  2160
ttctgttctg ctgaattttc tttcagatac atgtgaccga atagtagaaa gcctttgcaa  2220
atgcaagagc caacaacttt ggcgtctgcc atctgcacaa gcatccgatt taattgaaaa  2280
tgataaccat ggagttgatt tggatatgag gatagccagt gttcttcaaa gcacaggaca  2340
```

```
ccattatgat ggtgggtttt ggactgattt tgtgaagcct gagacaccgg aaaacaaaag    2400
gcatgtggca attgttacaa cagctagtct tccttggatg accggaacag ctgtaaatcc    2460
gctattcaga gcggcgtatt tggcaaaagc tgcaaaacag agtgttactc tcgtggttcc    2520
ttggctctgc gaatctgatc aagaactagt gtatccaaac aatctcacct tcagctcacc    2580
tgaagaacaa gagagttata tacgtaaatg gttggaggaa aggattggtt tcaaggctga    2640
ttttaaaatc tccttttacc caggaaaggt atgttgatca ttttggattc tatttttta    2700 tttctatggc tgccaatatg tttttcaatt atttctatag agtaactgag ctttctggtt    2760
tcttatagtt ttcaaaagaa aggcgcagca tatttcctgc tggtgacact tctcaattta    2820
tatcgtcaaa agatgctgac attgctatac ttgaagaacc tgaacatctc aactggtatt    2880
atcacggcaa gcgttggact gataaattca accatgttgt tggaattgtc cacacaaact    2940
acttagagta catcaagagg gagaagaatg gagctcttca agcattttt gtgaaccatg    3000 taaacaattg ggtcacacga gcgtattgtg acaaggtgaa tcatctactc tatttcttca    3060
agccttgttc tgttgcttga atcctcttta ctaataaata gtacgagc taatacatat    3120 tttctactca tgaaaggttc ttcgcctctc tgcggcaaca caagatttac caaagtctgt    3180
tgtatgcaat gtccatggtg tcaatcccaa gttccttatg attggggaga aaattgctga    3240
agagagatcc cgtggtgaac aagctttctc aaaaggtgca tacttcttag gaaaaatggt    3300
gtgggctaaa ggatacagag aactaataga tctgatggct aaacacaaaa gcgaacttgg    3360
gagcttcaat ctagatgtat atgggaacgg tgaagatgca gtcgaggtcc aacgtgcagc    3420
aaagaaacat gacttgaatc tcaatttcct caaggaagg gaccacgctg acgatgctct    3480
tcacaagtaa gttctgaaaa atgtgctttg ctttttaaaaa cttgttaagg tttcgctctt    3540
tgattgtctt tcccacatct tgatgaaggt acaaagtgtt cataaacccc agcatcagcg    3600
atgttctatg cacagcaacc gcagaagcac tagccatggg gaagtttgtg gtgtgtgcag    3660
atcacccttc aaacgaattc tttagatcat tcccgaactg cttaacttac aaaacatccg    3720
aagactttgt gtccaaagtg caagaagcaa tgacgaaaga gccactacct ctcactcctg    3780
aacaaatgta caatctctct tgggaagcag caacacagag gttcatggag tattcagatc    3840
tcgataagat cttaaacaat ggagagggag gaaggaagat gcgaaaatca agatcggttc    3900
cgagctttaa cgaggtggtc gatggaggat tggcattctc acactatgtt ctaacaggga    3960
acgatttctt gagactatgc actggagcaa caccaagaac aaaagactat gataatcaac    4020
attgcaagga tctgaatctc gtaccacctc acgttcacaa gccaatcttc ggctggtaga    4080
tatttcccca taggccaccc agttattgct tgtgacttat taaaccacta cgttattgtt    4140
atcctttttt acttttacag ttgttgtagg tcgtttgttt gttaatagaa agggtagatt    4200
attattagat gtcttttgt aaaatatcaa tacgaagcgt atttgatgat atataaaata    4260
actatattgg caaaaatatg aactatgaag gccgttttcg tgattttgtt cttttgtttc    4320
acgaattcaa gctattcccc ttttttttacg ccaaagatga aaagaaccct ccctattaat    4380
atcgctattg tctaaaattt cgaaaactac tttaatcacg actagaccaa atatatgtcg    4440
accgataccg atagagaaat tagtgccccg tctaatactt tctctccaaa attacagaat    4500
atttagagta gttaatcaac gtaacacgac aaggaaaatg atggaaaaag tggtggtttc    4560
tgctttggca actagtgtta ggtcacttac gtcctctttt tctgtattgg aaattacgtg    4620
gataaattga actttctttc aatctctatc aaattattaa tccacacatg tatacgcaat    4680
atatgatcat taaataaata aaagttaga ttggtctata aattcgtatc acaaatggac    4740
```

```
taataatttg tagtgaaaac tcatttaccc atgtgacagc tccaaatttc tgaacttttt    4800
attttgaggg atggtacaaa tccgagttcc atgatcatgg aaaaatcaaa tttaacaaac    4860
acaaattact gtttgaaaca agcaagttac tatatatgta gtttgatttc acactagaga    4920
atctactgat aatgaatttt ttatatatcg tgaagctgaa agtgaaatta taactagcta    4980
gttgaattgc ttattatggt tggagggag ccgatgaaaa attcttcgac cacacataaa    5040
gtcacctttc taaagaacac ttgcaccgac cacatcaatc acgcattcat aaattttcaa    5100
catttatata aatgtaggaa aaaaacaa                                       5128
```

<210> SEQ ID NO 6
<211> LENGTH: 5050
<212> TYPE: DNA
<213> ORGANISM: Arabidopsis thaliana
<220> FEATURE:
<221> NAME/KEY: mutation
<222> LOCATION: (334)
<223> OTHER INFORMATION: T to C exchange (5' non-transcribed region)
<221> NAME/KEY: mutation
<222> LOCATION: (3189)
<223> OTHER INFORMATION: C to T exchange (CAA to TAA, premature stop
      codon)
<221> NAME/KEY: mutation
<222> LOCATION: (3434)
<223> OTHER INFORMATION: G insertion after 3434 (silent, in intron)
<221> NAME/KEY: mutation
<222> LOCATION: (3649)
<223> OTHER INFORMATION: C to T exchange (conservative exchange,
      Ser codon)
<221> NAME/KEY: mutation
<222> LOCATION: (4795)
<223> OTHER INFORMATION: A insertion after 4795 (3' non-transcribed
      region)
<221> NAME/KEY: mutation
<222> LOCATION: (4868)
<223> OTHER INFORMATION: T to A exchange (3' non-transcribed region)
<221> NAME/KEY: mutation
<222> LOCATION: (4874)
<223> OTHER INFORMATION: A to T exchange (3' non-transcribed region)

<400> SEQUENCE: 6

```
ttttgtatga tatatatatg gtcaagatgg tgaagacaaa ggttctacta ttgtataatg     60
gtatcaaaat ttgctaaatt tctaacaatt tcacaaggtc tcgcgtggcg tccgttggtt    120
gttttggtta agtcggcctc tattttgatc cgttaatgga actcgttacg gtctaattac    180
gtccactgat atcactttcc aatgttttt tttgttaaat gtcattgtca ataccatgcc    240
ccgtaggacc agattcttcg attccagcat attcctaagt taaatccgac caaatcggat    300
aatctcgtca accactcaca acacgccacg taaccaatga tgtggaaccc atgccacgtt    360
ggacacggtc tcacgggaca aggcttcagt aaagagcgcc tatcgtccgt ccgacttgtt    420
tattttccac gtgttaatct tccagaataa tcagaaagag aattaaaaaa ataaaacaat    480
ccaaattaat ctcagccgtc aatttctctt cttcttcttc ccaaattctc tcaacagata    540
gagaaaacct tattagcagc actctcacga aatcgtcgtg acgaaacgat aaaccctaag    600
tcatggtaaa ggaaactcta attcctccgt catctacgtc aatgacgacc ggaacatctt    660
cttcttcgtc tctttcaatg acgttatcct caacaaacgc gttatcgttt ttgtcgaaag    720
gatggagaga ggtatgggat tcagcagatg cggatttgca gctgatgcga gacagagcta    780
actctgttaa gaatctagca tcaacgttcg atagagagat cgagaatttc ctcaataact    840
cggcgaggtc tgcgtttccc gttggttcac catcggcgtc gtctttctca aatgaaattg    900
gtatcatgaa gaagcttcag ccgaagattt cggagtttcg tagggtttat tcggcgccgg    960
```

-continued

```
agattagtcg caaggttatg gagagatggg gacctgcgag agcgaagctt ggaatggatc      1020
tatcggcgat taagaaggcg attgtgtctg agatggaatt ggatgagcgt cagggagttt      1080
tggagatgag tagattgagg agacggcgta atagtgatag ggttaggttt acggagtttt      1140
tcgcggaggc tgagagagat ggagaagctt atttcggtga ttgggaaccg attaggtctt      1200
tgaagagtag atttaaagag tttgagaaac gaagctcgtt agaatattg agtggattca       1260 agaacagtga atttgttgag aagctcaaaa ccagctttgt aagtttctcc aactttttgg      1320
gaacctattt caaaagtttc ttctatctta ctgtagaagt ggcttctctt tcaatagcca      1380
cgacattttc gtatgctgac ttgatagtta ctgttcttgg aatgattgat tgagtttctt      1440
atggtgtttg gcaacttttc taatggtgct ttttctttt gttttatttg cagaaatcaa       1500
tttacaaaga aactgatgag gctaaggttg gtatttggaa gttggagctc tatcagtttt      1560
tcttgttact ttatatattt ttaggtcgag ttcagtgttg gattgggagt ttaacttggc      1620
ctccttttac tttggtgcag gatgtccctc cgttggatgt acctgaactg ttggcatgtt      1680
tggttagaca atctgaacct tttccttgatc agattggtgt tagaaagggt aagattgcat     1740
ttttctcttc atgatggtta attattttgt ctgttgtatg tattgagttg tttctctacc      1800
ataggtggtt tttccgtcaa aagtttgaat cttctctctg atattagagt gtctttgtta      1860
agtgggttgc ttgcttcacc agaagtttag atggtgagat ttgatgttct gcattatcac      1920
actaatcctg gatatcaaat atgtgtaagt ctagattctg tatgagacag atcaatcaaa      1980
tgacatctgc cgtagacata aaatttcta gatgtgtagg ttattggttt taaacaccct       2040
ttcttgtaca ttatcttata gtttcagtgt ttacatacaa agttcctgat tctgttctgc      2100
tgaattttct ttcagataca tgtgaccgaa tagtagaaag cctttgcaaa tgcaagagcc      2160
aacaactttg gcgtctgcca tctgcacaag catccgattt aattgaaaat gataaccatg      2220
gagttgattt ggatatgagg atagccagtg ttcttcaaag cacaggacac cattatgatg      2280
gtgggttttg gactgatttt gtgaagcctg agacaccgga aaacaaaagg catgtggcaa      2340
ttgttacaac agctagtctt ccttggatga ccggaacagc tgtaaatccg ctattcagag      2400
cggcgtattt ggcaaaagct gcaaaacaga gtgttactct cgtggttcct tggctctgcg      2460
aatctgatca agaactagtg tatccaaaca atctcacctt cagctcacct gaagaacaag      2520
agagttatat acgtaaatgg ttggaggaaa ggattggttt caaggctgat tttaaaatct      2580 cctttaccc aggaaaggta tgttgatcat tttggattct atttttttat ttctatggct       2640
gccaatatgt ttttcaatta tttctataga gtaactgagc tttctggttt cttatagttt      2700
tcaaaagaaa ggcgcagcat atttcctgct ggtgacactt ctcaatttat atcgtcaaaa      2760
gatgctgaca ttgctatact tgaagaacct gaacatctca actggtatta tcacggcaag      2820
cgttggactg ataaattcaa ccatgttgtt ggaattgtcc acacaaacta cttagagtac      2880
atcaagaggg agaagaatgg agctcttcaa gcattttttg tgaaccatgt aaacaattgg      2940
gtcacacgag cgtattgtga caaggtgaat catctactct atttcttcaa gccttgttct      3000
gttgcttgaa tcctctttac taataaatag tacacgagct aatacatatt ttctactcat      3060
gaaaggttct tcgcctctct gcggcaacac aagatttacc aaagtctgtt gtatgcaatg      3120
tccatggtgt caatcccaag ttccttatga ttggggagaa aattgctgaa gagagatccc      3180
gtggtgaata agctttctca aaaggtgcat acttcttagg aaaaatggtg tgggctaaag      3240
gatacagaga actaatagat ctgatggcta aacacaaaag cgaacttggg agcttcaatc      3300
```

-continued

| | |
|---|---|
| tagatgtata tgggaacggt gaagatgcag tcgaggtcca acgtgcagca aagaaacatg | 3360 |
| acttgaatct caatttcctc aaaggaaggg accacgctga cgatgctctt cacaagtaag | 3420 |
| ttctgaaaaa tgtggctttg cttttaaaaa cttgttaagg tttcgctctt tgattgtctt | 3480 |
| tcccacatct tgatgaaggt acaaagtgtt cataaacccc agcatcagcg atgttctatg | 3540 |
| cacagcaacc gcagaagcac tagccatggg gaagtttgtg gtgtgtgcag atcacccttc | 3600 |
| aaacgaattc tttagatcat tcccgaactg cttaacttac aaaacatctg aagactttgt | 3660 |
| gtccaaagtg caagaagcaa tgacgaaaga gccactacct ctcactcctg aacaaatgta | 3720 |
| caatctctct tgggaagcag caacacagag gttcatggag tattcagatc tcgataagat | 3780 |
| cttaaacaat ggagagggag gaaggaagat gcgaaaatca agatcggttc cgagctttaa | 3840 |
| cgaggtggtc gatggaggat tggcattctc acactatgtt ctaacaggga acgatttctt | 3900 |
| gagactatgc actggagcaa caccaagaac aaaagactat gataatcaac attgcaagga | 3960 |
| tctgaatctc gtaccacctc acgttcacaa gccaatcttc ggctggtaga tatttcccca | 4020 |
| taggccaccc agttattgct tgtgacttat taaaccacta cgttattgtt atcctttttt | 4080 |
| acttttacag ttgttgtagg tcgtttgttt gttaatagaa agggtagatt attattagat | 4140 |
| gtcttttgt aaaatatcaa tacgaagcgt atttgatgat atataaaata actatattgg | 4200 |
| caaaaatatg aactatgaag gccgttttcg tgattttgtt cttttgtttc acgaattcaa | 4260 |
| gctattcccc ttttttacg ccaaagatga aagaaccct ccctattaat atcgctattg | 4320 |
| tctaaaattt cgaaaactac tttaatcacg actagaccaa atatatgtcg accgataccg | 4380 |
| atagagaaat tagtgccccg tctaatactt tctctccaaa attacagaat atttagagta | 4440 |
| gttaatcaac gtaacacgac aaggaaaatg atggaaaaag tggtggtttc tgctttggca | 4500 |
| actagtgtta ggtcacttac gtcctctttt tctgtattgg aaattacgtg gataaattga | 4560 |
| actttctttc aatctctatc aaattattaa tccacacatg tatacgcaat atatgatcat | 4620 |
| taaataaata aaaagttaga ttggtctata aattcgtatc acaaatggac taataatttg | 4680 |
| tagtgaaaac tcatttaccc atgtgacagc tccaaatttc tgaactttt attttgaggg | 4740 |
| atggtacaaa tccgagttcc atgatcatgg aaaaatcaaa tttaacaaac acaaaattac | 4800 |
| tgtttgaaac aggcaagtta ctatatatgt agtttgattt cacactagag aatctactga | 4860 |
| taatgaaatt tttttatatc gtgaagctga aagtgaaatt ataactagct agttgaattg | 4920 |
| cttattatgg ttggaggga gccgatgaaa aattcttcga ccacacataa agtcacctttt | 4980 |
| ctaaagaaca cttgcaccga ccacatcaat cacgcattca taaattttca acatttatat | 5040 |
| aaatgtagga | 5050 |

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence:
    Oligonucleotide primer

<400> SEQUENCE: 7
gcggatccgg taaaggaaac tctaatt                27

<210> SEQ ID NO 8
<211> LENGTH: 27
<212> TYPE: DNA
<213> ORGANISM: Artificial Sequence
<220> FEATURE:

```
-continued

<223> OTHER INFORMATION: Description of Artificial Sequence:
      Oligonucleotide primer

<400> SEQUENCE: 8
ttctgcagtc taccagccga agattgg                                         27
```

DNA ENCODING FOR PLANT DIGALACTOSYLDIACYLGLYCEROL GALACTOSYLTRANSFERASE AND METHODS OF USE

Priority is claimed to U.S. Provisional application No. 60/132,849, filed May 6, 1999.

SPONSORSHIP

Work on this invention was sponsored in part by Department of Energy Grant DE-FG02-98ER20305. The Government may have certain rights in the invention.

FIELD OF THE INVENTION

The invention relates generally to plant galactolipids and more particularly the gene encoding digalactosyldiacylglycerol galactosyltransferase.

BACKGROUND OF THE INVENTION

The process of photosynthesis is the basis for all life on earth because it provides oxygen and ultimately converts inorganic matter into organic matter. The photosynthetic apparatus in plant cells is associated with a particular membrane system inside chloroplasts, the thylakoids. Four lipids are found to be associated with thylakoid membranes in plants and photosynthetic bacteria. Only one of them is a phospholipid, the ubiquitous phosphatidylglycerol. The other three are non-phosphorous diacylglycerol glycolipids with one or two galactose moieties or a sulfonic acid derivative of glucose attached to diacylglycerol. Browse, J. et al., Ann. Rev. Plant Physiol. Plant Mol. Biol. 42:467 (1991); Joyard, J. et al., Plant Physiol. 118:715 (1998). The galactolipids constitute the bulk (close to 80%) of the thylakoid lipid matrix and within green plant parts, 70–80% of the lipids are associated with photosynthetic membranes. Taking into account that plants represent the major portion of the global bioorganic matter, it comes as no surprise that the two galactolipids, mono- and digalactosyldiacylglycerol, are the most abundant lipids in the biosphere. Most vegetables and fruits in human or animal diets are rich in galactolipids. Their breakdown products represent an important dietary source of galactose and polyunsaturated fatty acids. Ohlsson, L. et al., J. Nutrition 128:239 (1998); Andersson, L. et al., J. Lipid Res. 36:1392 (1995). The elucidation of the pathway for galactolipid biosynthesis has been extremely challenging. Thylakoid membrane lipid biosynthesis in plants is highly complex bringing together carbohydrate and fatty acid metabolisms. There is a mesmerising number of molecular species for each thylakoid lipid due to the large number of combinatorial possibilities for fatty acid substituents. Even more dazzling, the biosynthesis of thylakoid lipids is not restricted to enzymes associated with the chloroplast where galactolipids are found, but also involves enzymes in the endoplasmic reticulum (ER) (FIG. 1). The mechanism for subcellular trafficking of lipid moieties from the ER that ultimately become incorporated into the thylakoid lipids inside the plastids poses one of the most challenging enigmas of modern plant biochemistry. Molecular species of galactolipids containing diacylglycerol moieties derived from the plastid or the ER pathway can be distinguished based on their fatty acid composition. Heinz, E. et al., Plant Physiol. 72:273 (1983). Lipid moieties assembled inside the plastid carry preferentially a 16-carbon fatty acid in the sn2-position of diacylglycerol, while lipids derived from the ER pathway contain an 18-carbon fatty acid in this position. This is due to different substrate specificities of the respective acyltransferases in the plastid and the ER. An extensive screening of different plant species revealed that the plastid pathway is dispensable in many plants. Mongrand, S. et al., Phytochemistry 49:1049 (1998). However, no naturally occurring plant has been found, in which the ER pathway was non-functional. A mutant of Arabidopsis, act1, is partially blocked in the plastid pathway. Kunst, L. et al., PNAS (USA) 85:4143 (1988). This mutant is deficient in the acyltransferase which catalyses the biosynthesis of lysophosphatidic acid inside the plastid (FIG. 1). Other mutants of Arabidopsis have been described that affect the fatty acid and, thus, the molecular species composition of thylakoid lipids. Browse, J. et al., in Arabidopsis, E. M. Meyerowitz and C. R. Somerville, Eds. (Cold Spring Harbor Laboratory Press, N.Y.) pp. 881–912 (1994). Most of these are deficient in fatty acid desaturases. However, the only higher plant mutant known to be directly affected in galactolipid assembly is the dgd1 mutant of Arabidopsis. Dormann, P. et al., Plant Cell 7:1801 (1995). In this mutant the relative amount of the digalactosyl lipid is reduced to 10% of wild type. It has already proven to be very valuable in assessing the importance of the digalactosyl lipid for the assembly and function of the photosynthetic membranes. Growth, chloroplast ultra structure, the composition and relative ratios of different pigment protein complexes, the light utilization by the photosynthetic apparatus, and the import of proteins into chloroplasts are affected in the dgd1 mutant. Hartel, H. et al., Plant Physiol. 115:1175 (1997); Reifarth, F. et al., Biochemistry 36:11769 (1997); Hartel, H. et al., Plant Physiol. Biochem. 36:407 (1998); Chen, L.-J. et al., Plant J. 16:33 (1998). In addition to the reduction in the amount of galactolipid, the dgd1 mutant also shows a peculiar alteration in the fatty acid composition of the monogalactosyl lipid with a characteristic increase in the amount of molecular species containing 18-carbon fatty acids. The accumulation of these molecular species of the monogalactosyl lipid is consistent with their presumed precursor function in the biosynthesis of the digalactosyl lipid. Based on labelling experiments with isolated chloroplasts (van Besouw, A. et al., Biochim. Biophys. Acta 529:44 (1978); Hemmskerk, J. W. M. et al., Plant Physiol. 93:1286 (1990)), it has been proposed that one galactose moiety is transferred from one monogalactosyl lipid onto a second to form the digalactosyl lipid (FIG. 1). The released diacylglycerol moiety is made available for further thylakoid lipid assembly with the bulk appearing in monogalactosyl lipid. As can be assumed from the fatty acid composition of the digalactosyl lipid in the wild type (Browse, J. et al., Biochem. J. 235:25 (1986)), the responsible enzyme is specific for molecular species derived from the ER. Accordingly, approximately equal amounts of ER-derived molecular species are found in the digalactosyl and monogalactosyl lipids (FIG. 1). Therefore, it is expected that the disruption of digalactosyl lipid biosynthesis in the dgd1 mutant also disturbs the assembly of other thylakoid lipids, in particular the ER-derived monogalactosyl lipid.

It would thus be desirable to provide the wild-type DGD1 gene encoding for digalactosyldiacylglycerol galactosyltransferase (DGD1). It would also be desirable to isolate and purify the gene product. It would be further desirable to provide in vitro and in vivo assays to screen for new herbicides that inhibit the DGD1 gene product. Galactolipids are unique to plants and other photosynthetic organisms. Therefore, in contrast to most herbicides currently in use, herbicides that inhibit galactolipid biosynthesis will not be toxic to animals, humans or microbial organisms in the soil.

It would also be desirable to control the digalactosyldiacylglycerol levels in plants by controlling the expression of the gene encoding for the DGD1 protein. It would further be desirable to transform plants using the gene in order to alter their lipid composition. An alteration in lipid composition would provide plants with an increased resistance to environmental factors such as, but not limited to, temperature stress and/or pathogen infection. It would further provide an increase in the yield of crop plants such as leafy vegetables.

SUMMARY OF THE INVENTION

The present invention provides a novel purified and isolated nucleic acid sequence encoding digalactosyldiacylglycerol galactosyltransferase (DGD1). The cDNA encoding DGD1 is set forth SEQ ID NO: 1. The deduced amino acid sequence of DGD1 is also provided and set forth in SEQ ID NO: 2. The protein has a predicted molecular weight of 91.8 kDa and has some sequence similarity in the C-terminal portion to bacterial and plant glycosyltransferases.

Methods for making and using the cDNA encoding DGD1 are also provided. For example, wild-type DGD1 can be used to produce recombinant DGD1 in bacteria or yeast. Such recombinant protein can be used in either an in vivo or in vitro assay to screen compounds for new herbicides. Additionally, DGD1 may be used to alter a plant's leaf lipid composition thus altering sensitivity to environmental factors such as, but not limited to, temperature stress and/or pathogen infection and, in some cases, increase the yield of crop plants. Expression vectors containing the cDNA, transgenic plants and other organisms, e.g., *E. coli*, transfected with said vectors, as well as seeds from said plants, are also provided by the present invention.

Additional objects, advantages, and features of the present invention will become apparent from the following description, taken in conjunction with the accompanying drawings.

BRIEF DESCRIPTION OF THE DRAWINGS

The various advantages of the present invention will become apparent to one skilled in the art by reading the following specification and by referencing the following drawings in which.

DETAILED DESCRIPTION OF THE PREFERRED EMBODIMENTS

Figure 1:
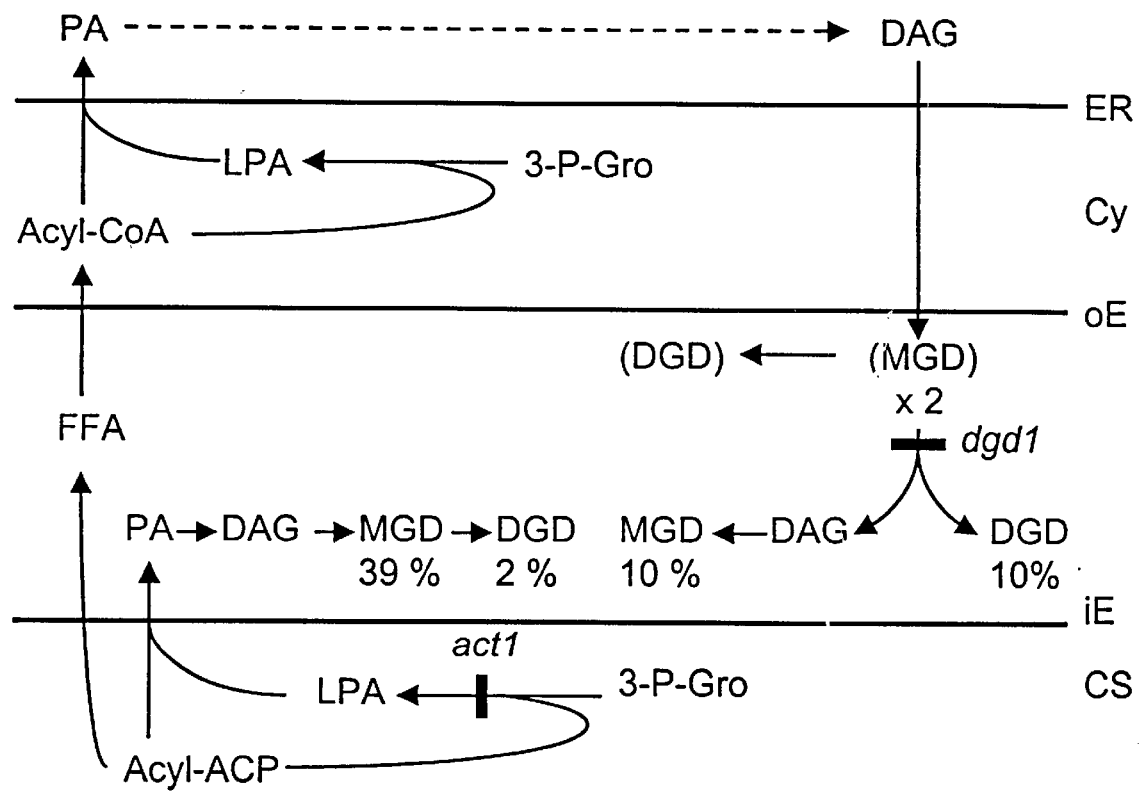
FIG. 1 is a schematic illustrating galactolipid biosynthesis in Arabidopsis.

The cDNA sequence encoding digalactosyldiacylglycerol galactosyltransferase (DGD1) is set forth in SEQ ID NO: 1. The deduced amino acid sequence is provided in SEQ ID NO: 2. The protein has a predicted mass of 91.8 kDa. Sequence comparisons show some similarity in the C-terminal portion to bacterial and plant glycosyltransferases.

A method for producing DGD1 in a host cell is also provided in the present invention. The method includes the steps of introducing an expression vector comprising a cDNA encoding DGD1 or a functional mutant thereof into a host cell and expressing the cDNA in an amount sufficient to permit purification of the DGD1. A vector may include a promoter that is functional in either a eukaryotic or prokaryotic cell. Preferably, the vector is introduced into a prokaryotic cell, such as *E. coli* that is routinely used for production of recombinantly produced proteins. Alternatively, the vector is introduced into a eukaryotic cell, such as *Saccharomyes cerevisiae* (yeast), that is also routinely used for the production of recombinantly produced proteins. It is further contemplated that DGD1 may be manufactured using standard synthetic methods.

The availability of large amounts of recombinant protein will permit the rapid screening of compounds to identify new herbicides. It will be appreciated that either a cell lysate, partially purified or purified recombinant DGD1 can be used in both in vitro and in vivo screening assays. It will also be appreciated that purified protein from a plant such as Arabidopsis is also contemplated within the present invention, and can also be used to screen for new compounds. For example, galactosyltransferase activity assay is provided wherein the amount of digalactosyldiacylglycerol (DGD) produced in *E. coli* expressing recombinant DGD1 and monogalactosyldiacylglycerol synthase is determined by thin layer chromatography. Thus, in a preferred embodiment, the polar lipids are extracted from the *E. coli* cells with one volume of 1M KCl and 0.2M $H_3PO_4$ and 2 volumes of methanol/chloroform (1:1, v/v). In another embodiment, the extracted polar lipids are separated by thin layer chromatography on ammonium sulfate-impregnated silica plates developed in acetone/toluene/water (90:30:8, v/v/v/). DGD lipid is then visualized by staining with α-naphthol. It will be appreciated that *E. coli* expressing recombinant DGD1 can be exposed to various compounds and the effect of such treatment on DGD production assessed.

Once a compound is identified as an inhibitor of DGD1, mutagenesis can be used to create DGD1 mutants that show decreased or no sensitivity to the inhibitory compound. DGD1 mutants can be made by known methods such as, but not limited to, site-directed mutagenesis or random mutagenesis, followed by screening for an active DGD1 mutant. It will be appreciated that such a mutant gene would be suitable for overexpression in crop plants, conferring resistance to the selected inhibitor compound.

Furthermore, sequences of the present invention may be used to alter a plant's leaf lipid composition. Naturally-selected mutants of Arabidopsis with either decreased or increased expression of DGD1 show altered lipid and fatty acid composition. Altering a plants leaf lipid composition can increase a plant's resistance to environmental factors such as, but not limited to, heat and/or cold stress, increase resistance to pathogen infection, and/or increase crop yield, especially of leafy vegetables such as lettuce. The method of altering leaf lipid composition of a plant includes the steps of introducing an expression vector comprising a cDNA encoding DGD1 or a functional mutant thereof, operably linked to a promoter functional in a plant cell into the cells of plant tissue and expressing the encoded protein in an amount effective to alter the leaf lipid composition. The level of expression can be increased by either combining the cDNA with a promoter that provides for a high level of expression, or by introducing multiple copies into the cell so that multiple copies are integrated into the genome of transformed plant cells. Once. transformed cells exhibiting increased DGD1 activity are obtained, transgenic plants and seeds can then be regenerated therefrom, and evaluated for the stability of the inheritance of altered leaf lipid composition.

The DGD1 nucleotide sequence may thus be fused to a gene or fragment thereof, which allows it to be expressed in a plant cell. The DGD1 nucleotide sequence in combination with the gene or gene fragment, is referred to as an "expression vector" herein. It will be appreciated that the expression vectors of the present invention may contain any regulatory elements necessary and known to those skilled in the art for expression of DGD1. For example, such vectors may contain, but are not limited to, sequences such as promoters, operators and regulators, which are necessary for, and/or may enhance, the expression of DGD1.

The invention also provides the nucleic acid sequence from a shorter gene on chromosome 4 of *Arabidopsis thaliana* that has a high sequence similarity to DGD1 (blast P score of 360). The nucleic acid sequence, DGD2, is set forth in SEQ ID NO: 3 (GenBank Accession No. AF058919). The deduced amino acid sequence DGD2 is provided in SEQ ID NO: 4. The gene, DGD2 encodes a protein missing approximately 340 amino acids of the N-terminal portion as compared to DGD1, but shows similarity to the glycosyltransferase-like sequence part of DGD1. The amino acid sequence homology between DGD1 and DGD2 is 64.4% over 365 amino acids. This high degree of homology indicates that DGD2 would have the same activity and a similar function as DGD1 in plants. Therefore, it will be appreciated that the DGD2 gene can be used with the methods of the present invention. The predicted DGD1 protein contains an N-terminal transit peptide typical for proteins imported into the plastid. Furthermore, two strongly hydrophobic domains (amino acids 347–372 and 644–670) were found in the sequence. While not wishing to be bound by theory, this observation agrees with a proposed association of DGD1 with the plastid envelope membranes. Block, M. A. et al., *J. Biol. Chem.* 258:13281 (1983); Cline, K. et al., *Plant Physiol.* 71:366 (1983); Dorne, A.-J. et al., *FEBS Lett.* 145:30 (1982).

As referred to herein, the term "cDNA" is meant a nucleic acid, either naturally occurring or synthetic, which encodes a protein product. The term "nucleic acid" is intended to mean natural and/or synthetic linear, circular and sequential arrays of nucleotides and nucleosides, e.g., cDNA, genomic DNA (gDNA), mRNA, and RNA, oligonucleotides, oligonucleosides, and derivatives thereof. The term "encoding" is intended to mean that the subject nucleic acid may be transcribed and translated into either the desired polypeptide or the subject protein in an appropriate expression system, e.g., when the subject nucleic acid is linked to appropriate control sequences such as promoter and enhancer elements in a suitable vector (e.g., an expression vector) and when the vector is introduced into an appropriate system or cell. As used herein, "polypeptide" refers to an amino acid sequence which comprises both full-length protein and fragments thereof.

As referred to herein, the term "capable of hybridizing under high stringency conditions" means annealing a strand of DNA complementary to the DNA of interest under highly stringent conditions. Likewise, "capable of hybridizing under low stringency conditions" refers to annealing a strand of DNA complementary to the DNA of interest under low stringency conditions. In the present invention, hybridizing under either high or low stringency conditions would involve hybridizing a nucleic acid sequence (e.g., the complementary sequence to SEQ ID No. 1 or portion thereof), with a second target nucleic acid sequence. "High stringency conditions" for the annealing process may involve, for example, high temperature and/or lower salt content, which disfavor hydrogen bonding contacts among mismatched base pairs. "Low stringency conditions" would involve lower temperature, and/or higher salt concentration than that of high stringency conditions. Such conditions allow for two DNA strands to anneal if substantial, as is the case among DNA strands that code for the same protein but differ in sequence due to the degeneracy of the genetic code. Appropriate stringency conditions which promote DNA hybridization, for example, 6X SSC at about 45° C., followed by a wash of 2X SSC at 50° C., are known to those skilled in the art or can be found in *Current Protocols in Molecular Biology*, John Wiley & Sons, N.Y. (1989), 6.31–6.3.6. For example, the salt concentration in the wash step can be selected from a low stringency of about 2X SSC at 50° C., to a high stringency of about 0.2X SSC at 50° C. In addition, the temperature in the wash step can be increased from low stringency at room temperature, about 22° C., to high stringency conditions, at about 65° C. Other stringency parameters are described in Maniatis, T., et al., *Molecular Cloning: A Laboratory Manual*, Cold Spring Harbor Laboratory Press, Cold Spring N.Y., (1982), at pp. 387–389; see also Sambrook J. et al., *Molecular Cloning: A Laboratory Manual*, Second Edition, Volume 2, Cold Spring Harbor Laboratory Press, Cold Spring, N.Y. at pp. 8.46–8.47 (1989).

The foregoing and other aspects of the invention may be better understood in connection with the following examples, which are presented for purposes of illustration and not by way of limitation.

SPECIFIC EXAMPLE 1

Construction of act1, dgd1 Double Mutant

Figure 2:
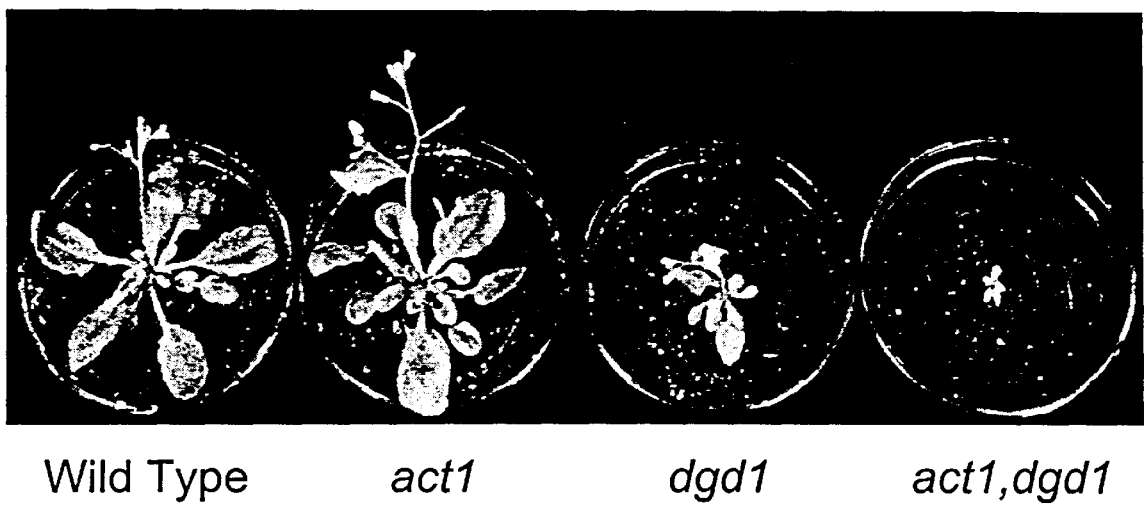
FIG. 2 is a photograph of four-week old Arabidopsis plants showing the appearance of the wild type, act1, dgd1 and act1, dgd1 double mutants.

An act1,dgd1double mutant (FIG. 1) was constructed. An $F_2$ population of plants derived from the cross of act1 (Arabidopsis Biological Resource Center, Columbus, Ohio) and dgd1 was screened by thin-layer and gas chromatography for the characteristic lipid and fatty acid phenotype anticipated for the double mutant. About 1/16 of the F2 plants contained strongly reduced amounts of 7,10,13-hexadecatrienoic acid as found in the act1 mutant and reduced amounts of the galactolipid DGD, indicative for the dgd1 mutation. This was the expected result for the segregation of two recessive unlinked mutations. Four-week-old representative plants raised on soil of the wild type (ecotype Col-2), the single homozygous mutants act1 and dgd1, and the act1, dgd1 double homozygous mutant are shown in FIG. 2. The double mutant was severely stunted (FIG. 2), and showed a more extreme growth phenotype than each of the mutant parents and any other known lipid mutant of Arabidopsis. The fatty acid composition of the galactolipids of the mutants as well as their fraction of total polar lipids were measured in leaves obtained from tissue-culture grown plants by thin-layer chromatography and subsequent gas chromatography of fatty acid methyl esters (Table 1).

|  | Wild Type[a] | dgd1[a] | act1[a] | act1,dgd1[a] |
|---|---|---|---|---|
| Monogalactosyldiacylglycerol | 49.8 | 53.5 | 53.7 | 44.2 |
| 7,10,13-hexadecatrienoic acid | 28.9 | 14.1 | 0.8 | 0.7 |
| α-linolenic acid | 62.5 | 78.5 | 88.5 | 86.4 |
| Digalactosyldiacylglycerol | 12 | 1.7 | 15.9 | 2.1 |
| 7,10,13-hexadecatrienoic acid | 2.6 | 2.8 | n.d. | n.d. |
| α-linolenic acid | 71.1 | 41.2 | 83.0 | 44.6 |

-continued

| | Wild Type[a] | dgd1[a] | act1[a] | act1,dgd1[a] |

[a]The values are given in mol % of total polar leaf lipids for the two galactolipids and mol % of fatty acids attached to each of the two galactolipids for 7,10,13-hexadecatrienoic acid (all-cis-16:3$\Delta^{7,10,13}$) and α-linolenic acid (all-cis-18:3$\Delta^{9,12,15}$). The values represent the means of three measurements each. The standard deviation was below 2.5% (galactolipids) and 1.0% (fatty acids). n.d., not detectable.

Because the lipid and fatty acid composition of the double mutant was not more severe than that of either of the parents, it is unlikely that the extreme growth phenotype of the double mutant is due to specific lipid or fatty acid effects. Thus, it seems plausible to conclude that the double mutant cannot produce sufficient amounts of thylakoid membranes, because the plastid pathway is affected by the act1 mutation and the ER pathway by the dgd1 mutation. A pathway model consistent with the available biochemical data and the single and double mutant phenotypes is shown in FIG. 1. For clarity, the model focuses on the galactolipids representing close to 80% of all thylakoid lipids. At least two genes encoding putative monogalactosyl lipid synthases are present in Arabidopsis (Shimojima, M. et al., *PNAS (USA)* 94:333 (1997); and it is proposed that these have different substrate specificities and different association with the inner or outer envelope in accordance with previous studies. Block, M. A. et al., *J. Biol. Chem.* 258:13281 (1983); Cline, K. et al., *Plant Physiol.* 71:366 (1983). This enzyme class is currently under investigation by others. Shimojima, M. et al., *PNAS (USA)* 94:333 (1997); Teucher, T. et al., *Planta* 184:319 (1991); Marechal, E. et al., *Biol. Chem.* 269:5788 (1994). Accordingly, a transient pool of monogalactosyl lipid is produced at the outer envelope from ER-derived diacylglycerol and immediately converted by DGD1. This process is accompanied by a transfer of lipid moieties from the outer to the inner envelope. In the absence of DGD1, monogalactosyl lipid cannot be efficiently synthesized via the ER-pathway but the plastid pathway can compensate for this deficiency. Only when both pathways are blocked as in the act1,dgd1 double mutant, the overall galactolipid biosynthesis is reduced to levels insufficient to support growth. Apparently, the proposed initial biosynthesis of galactolipids at the outer envelope membrane cannot compensate for the biosynthesis via DGD1, but would explain the small amount of digalactosyl lipid and the altered molecular species composition of monogalactosyl lipid in the dgd1 mutant.

SPECIFIC EXAMPLE 2

Isolation and Purification of the Gene Encoding DGD1

Figure 3A:
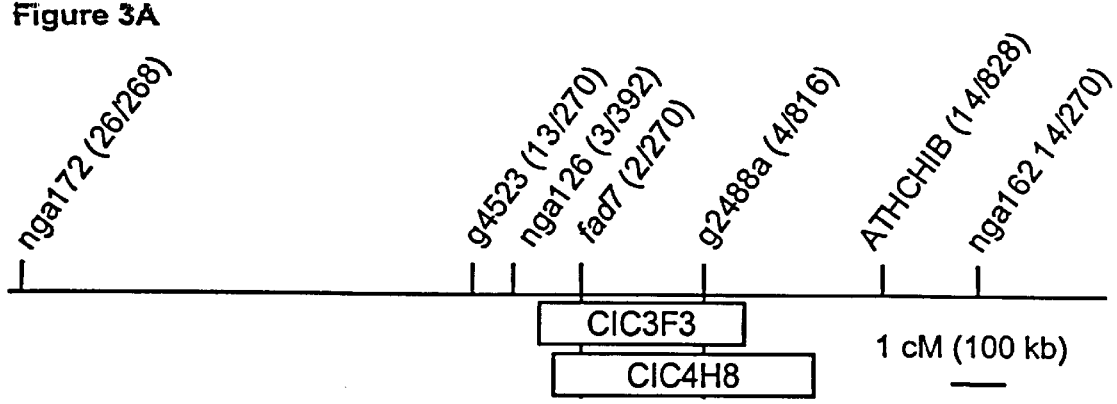
FIGS. 3A–3D are schematics illustrating the map-based cloning of the DGD1 gene.
Figure 3B:
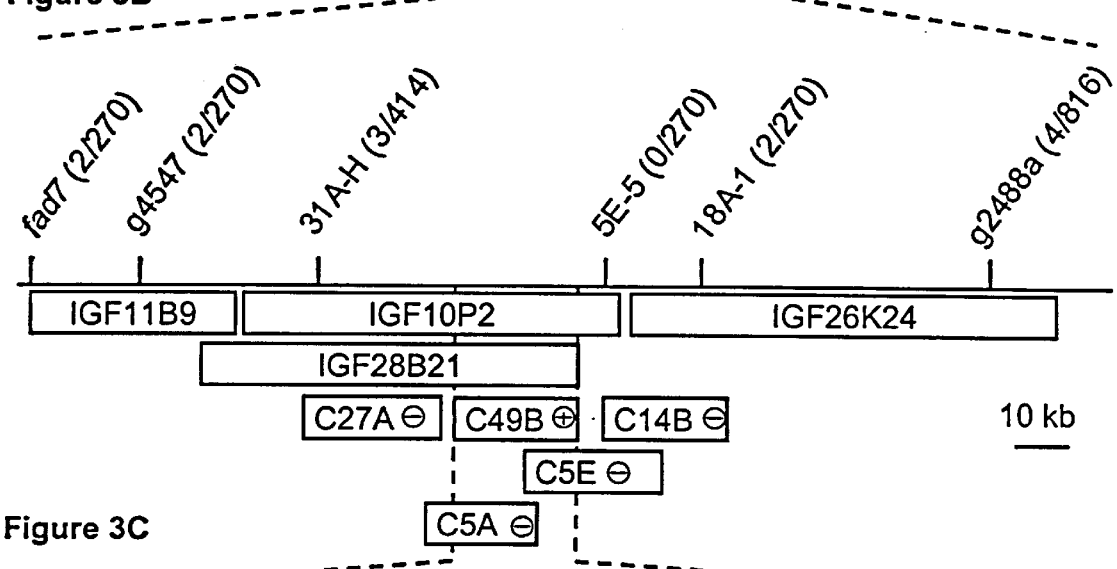
Figure 3C:
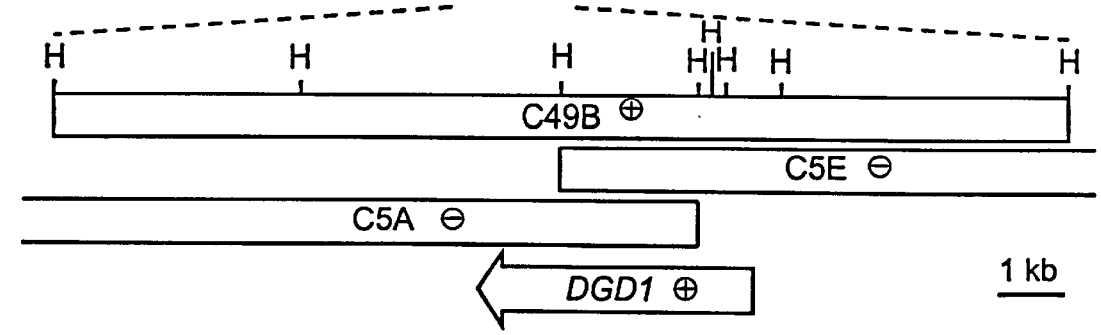
Figure 3D:
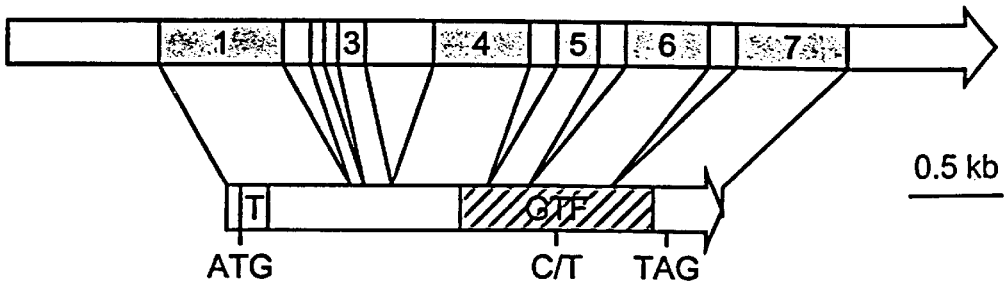

While the analysis of the dgd1 mutant and the act1,dgd1 double mutant in Specific Example 1 revealed the crucial role of DGD1 in galactolipid biosynthesis and subcellular lipid trafficking in higher plants, only the molecular and biochemical analysis of the dgd1 gene product will yield a true understanding of the underlaying mechanism. The cloning of both the mutant dgd1 and wild-type DGD1 genes represents the first step in this direction. Because no molecular information was available, the dgd1 locus and the corresponding dgd1 cDNA was isolated by a strategy based on the map position of dgd1. One of the difficulties encountered was the heterogeneous genetic background in the dgd1 mutant with markers characteristic for ecotypes Col-2 or Ler found interspersed around the dgd1 locus. This problem was solved by integration of two different mapping populations derived from crosses of dgd1 to Col-2 or Ler wild-type. From a total of 135 $F_2$ plants derived from the cross $dgd_1 \times Col-2$, plants with cross-overs between the two PCR markers nga162 and nga172 were selected. Bell, C. J. et al., *Genomics* 19:137 (1994). In this $F_2$ population, the dgd1 locus was mapped relative to the RFLP markers g4523, fad7, g4547, 5E-5 and 18A-1. Similarly, a total of 424 $F_2$ plants from the cross dgd1×Ler were screened for cross-overs between the PCR markers nga127 and ATHCHIB. This mapping population was used to score the RFLP markers g2488a and 31A-H. The RFLP markers were obtained from the Arabidopsis Biological Resource Center at Columbus, Ohio (g4523, fad7, g2488a, g4547) or from genomic fragments (31A–H, 5E-5, 18A-1) isolated from cosmid inserts in this study. Unambiguous scoring of the mutant phenotype had to be done by thin-layer chromatography of leaf lipid extracts, requiring several thousand samples to be processed during the fine mapping process. The map encompassing the DGD1 locus and the YAC, BAC, and cosmid contigs spanning the locus on chromosome three are shown in FIG. 3. FIG. 3A shows the genetic map of the relevant part of Arabidopsis chromosome 3. Two YAC clones containing dgd1 are shown. Numbers indicate recombinations between a given marker and dgd1 per number of chromosomes analyzed in the respective mapping population. FIG. 3B shows the fine mapping between the markers fad7 and g2488a. The BAC (IGF clone#) and cosmid (C clone#) contigs are shown. Complementing clones are marked by ⊕, non-complementing by –. FIG. 3C is a map of the cosmids C49B, C5A and C5E with H indicating HindIII restriction sites. Finally, FIG. 3D shows the structure of the DGD1 gene and cDNA. The exons are shaded and numbered 1 to 7. The sequence predicted to be a chloroplast transit peptide (T) is indicated, as well as the part showing similarity to glycosyltransferases (GTF, cross hatched), the start and stop codon (ATG, TAG, respectively), and the C to T mutation observed in the dgd1 mutant. Genomic DNA isolated from the markers fad7, g4547 and g2488a was used to isolate DNA fragments from different libraries (CIC Yeast Artificial Chromosome library (Camilleri, C. et al., *Plant J.* 14:633 (1998)); IGF Bacterial Artificial Chromosome library (Mozo, T. et al., *Mol. Gen. Genet.* 258:562 (1998)); Arabidopsis cosmid library (Meyer, K. et al., in *Genome Mapping in Plants*, A. H. Patterns, Ed. (Academic Press, N.Y., 1996), pp. 137–154). Different cosmids harbouring inserts between T-DNA borders were tested for complementation. Because the dgd1 mutant could not be transformed with these large genomic fragments, the clones were transferred into the wild type first and crossed the T-DNA into the dgd1 mutant. Cosmid clones were transferred into *Agrobacterium tumefaciens* C58C1 (pGV2260) and used to transform *Arabidopsis thaliana* Col-2 wild type plants via vacuum infiltration (Bechtold, N. et al., *Acad. Sci. Paris Life Sci.* 316:1194 (1993); Bent, A. F. et al., *Science* 265:1856 (1994)). Transformants were crossed with dgd1 mutant plants and the segregation pattern in the $F_2$ generation was analyzed. Complementation was assumed when of 100 tested $F_2$ plants carrying the T-DNA all were phenotypically wild-type, whereas in non-complementing lines, a segregation of the wild-type versus mutant phenotype of 3:1 was expected. A minimum of 100 transgenic $F_2$ plants derived from each cross (1 to 3 independent crosses per cosmid) were analyzed. To avoid the possibility that the construct was corrupted by chance in any particular plant, several independent transgenic lines were used. The analysis of three $F_2$ populations derived from crosses with independent lines containing cosmid C49B was consistent with genetic complementation by a gene encompassed by the insert.

Several cosmids overlapping (C5A, C5E) or neighbouring C49B (C27A, C14B) did not complement the mutation. Large portions of the cosmid C49B were sequenced (SEQ ID NO: 5). One putative gene was located in the centre of C49B, but was only partially contained by the cosmids C5A and C5E. Based on the complementation analysis for the cosmids C49B, C5A and C5E it was concluded that this gene represents the DGD1 locus. Therefore, the insert of C49B was used to screen a cDNA library. Uwer, U. et al. *Plant Cell* 10:1277 (1998). A 2683 bp long cDNA was identified and sequenced (FIG. 3D and SEQ ID NO: 1). This cDNA appeared to be complete because it contained in-frame stop codons 5'-prime of a putative ATG start codon. The cDNA was inserted behind a CaMV 35S promoter and transferred directly into the mutant by Agrobacterium mediated in planta transformation. For direct complementation analysis, the DGD 1 cDNA released from pBluescriptIISK(+) with SmaI, XhoI was ligated into the SmaI, SalI sites of the binary vector pBINAR-Hyg (Becker, D., *Nucl. Acids Res.* 18:203 (1990)) in sense orientation behind the CaMV 35S promoter. This construct was directly transferred into the dgd1 mutant via Agrobacterium by vacuum infiltration. Two transgenic plants were recovered which were phenotypically wild type with regard to habitus and lipid composition indicating complementation. To obtain corroborating evidence for complementation and to exclude the possibility of wild-type contamination, genetically homozygous dgd1 plants were identified in each complementation experiment by DNA/DNA hybridization using the RFLP marker 5E-5 which scores identical in the Col-2 and Ler wild type background but different in the dgd1 mutant. These plants were tested for lipids. With no exception, cosmid C49B and the DGD1 cDNA lead to wild-type lipid composition in all tested transgenic plants homozygous for dgd1. To obtain independent evidence for the identity of the DGD1 locus, the respective genomic DNA of the wild-type DGD1 and the mutant dgd1 loci were sequenced (SEQ ID NOS: 5 and 6). Further comparison of the genomic and cDNA sequences revealed 7 exons and a transition of a CAA codon (glutamine) to TAA in exon 6 in the dgd1 mutant gene leading to a premature stop codon.

SPECIFIC EXAMPLE 3

Reconstitution of the Plant Galactolipid Biosynthetic Pathway in *E. coli*

Figure 4:
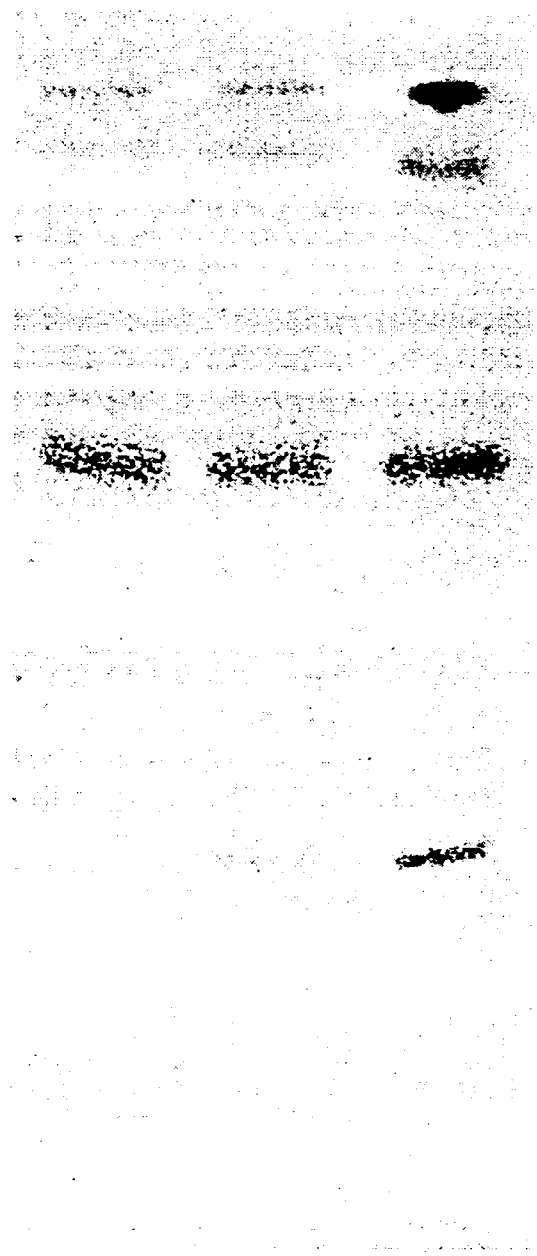
FIG. 4 is a photograph of a thin-layer chromatograph showing reconstitution of the plant galactolipid biosynthetic pathway in *E. coli*.

The DGD1 cDNA is predicted to encode a 91.8 kDa protein with some sequence similarity in the C-terminal portion to bacterial and plant glycosyltransferases. To determine the biosynthetic activity of the wild-type DGD1 gene product, the DGD1 cDNA was expressed in *E. coli* along with the monogalactosyldiacylglycerol (MGD) synthase previously isolated from cucumber. Shimojima, M. et al., *PNAS (USA)* 94:333 (1997). A 459 bp XhoI, PvuII fragment including the expression cassette was isolated from pQE31 (Qiagen Inc.) and ligated into the SalI, EcoRV sites of pACYC184 (Chang, A. C. Y. et al., *J. Bacteriol.* 134:1141 (1978)) giving rise to the plasmid pACYC-31. The open reading frame of the DGD1 cDNA was amplified by PCR using the primers 5'-GCGGATCCGGTAAAGGAAACTCTAATT-3' (Ben239; SEQ ID NO: 7) and 5'-TTCTGCAGTCTACCAGCCGAAGATTGG-3' (Ben241; SEQ ID NO: 8), thereby introducing a BamHl site at the 5' and a PstI site at the 3' terminus. This cDNA fragment was ligated into the corresponding restriction sites of pACYC-31. The resulting vector, pACYC-31/239, was transferred into XL1-Blue cells carrying the expression vector pGEX-3X with the cucumber MGD synthase cDNA (Shimojima et al. 1998). The cells were grown and protein expression induced with IPTG. The QIA expressionist: A handbook for high-level expression and purification of 6x His-tagged proteins. Qiagen, Inc., Valencia, Calif. (1997). The polar lipids were extracted from the *E. coli* cells with 1 volume 1 M KCl, 0.2 M $H_3PO_4$ and 2 volumes methanol/chloroform (1:1, v/v). Polar lipids were then separated by thin-layer chromatography on ammonium sulfate (0.15 M) impragnated Baker Si250PA silica plates developed in acetone/toluene/water (90:30:8, v/v/v). Digalactosyldiacylglycerol was visualized by staining with α-naphthol. In addition to MGD a new glycolipid was observed (Lane 2, FIG. 4) that co-migrates with an authentic digalactosyldiacylglycerol (DGD) standard (Lane 3, FIG. 4). In contrast, when the MGD synthase gene but not the dgd1 cDNA was present, no DGD was observed (Lane 1, FIG. 4). The plant galactolipid biosynthetic pathway was therefore, reconstituted in *E. coli*. Furthermore, this result demonstrates that the dgd1 gene indeed encodes a DGD galactosyltransferase.

A gene essential for the biosynthesis of the thylakoid lipid digalactosyldiacylglycerol was isolated from Arabidopsis by map-based cloning. The act1,dgd1 double mutant analysis strongly suggests that DGD1 also plays a critical role in lipid trafficking of ER-derived thylakoid lipids in higher plants. The availability of the wild-type DGD1 gene, the similar DGD2 gene, as well as genes encoding monogalactosyl lipid synthases of Arabidopsis will permit the rigorous testing of the current hypothesis for galactolipid biosynthesis and subcellular lipid trafficking described herein.

The foregoing discussion discloses and describes merely exemplary embodiments of the present invention. One skilled in the art will readily recognize from such discussion, and from the accompanying drawings, that various changes, modifications and variations can be made therein without departing from the spirit and scope of the invention.

Patent and literature references cited herein are incorporated by reference as if fully set forth.

We claim:

1. An isolated recombinant nucleic acid molecule comprising a sequence encoding an Arabidopsis digalactosyldiacylglycerol galactosyltransferase.

2. The nucleic acid molecule of claim 1, wherein said molecule comprises the sequence as set forth in SEQ ID NO: 1.

3. The nucleic acid molecule of claim 1, wherein the digalactosyldiacylglycerol galactosyltransferase comprises a sequence as set forth in SEQ ID NO: 2.

4. A vector comprising the nucleic acid of claim 1.

5. A host cell comprising the vector of claim 4.

6. The host cell of claim 5, wherein the host cell is a plant cell.

7. An isolated nucleic acid molecule comprising a nucleotide sequence capable of hybridizing under stringent conditions to a nucleic acid of claim 1 or complement thereof, wherein the isolated nucleic acid molecule encodes a polypeptide having digalactosyldiacylglycerol galactosyltransferase activity.

8. The nucleic acid of claim 7, wherein the nucleic acid molecule is capable of changing the lipid composition of a plant cell.

9. A vector comprising the nucleic acid of claim 8.

10. A host cell comprising the vector of claim 9.

11. The host cell of claim 10, wherein the host cell is a plant cell.

12. A method for producing a digalactosyldiacylglycerol galactosyltransferase, the method comprising:
   a) providing a host cell of claim 5; and
   b) growing the host cell, whereby the host cell produces the polypeptide.

13. The method of claim 12, wherein the host cell is an *E. coli*.

14. The method of claim 12, wherein the host cell is a yeast cell.

15. A method for altering leaf lipid composition in a plant, the method comprising introducing a nucleic acid molecule comprising a sequence encoding an Arabidopsis digalactosyldiacylglycerol galactosyltransferase.

16. The method of claim 15 wherein the nucleic acid molecule comprises SEQ ID NO: 1.

17. The method of claim 15, wherein the nucleic acid molecule comprises SEQ ID NO: 3.

18. A transgenic plant comprising the nucleic acid molecule of claim 1.

19. A transgenic seed comprising the nucleic acid molecule of claim 1.

* * * * *

UNITED STATES PATENT AND TRADEMARK OFFICE
CERTIFICATE OF CORRECTION

PATENT NO.    : 6,642,436 B1
DATED         : November 4, 2003
INVENTOR(S)   : Christoph Benning and Peter Döermann It is certified that error appears in the above-identified patent and that said Letters Patent is hereby corrected as shown below:

Column 4,
Line 63, "Once." should be -- Once --.

Column 8,
Line 3, "$dgd_1$ x Col-2" should be -- dgd1 x Col-2 --.

Signed and Sealed this

Thirty-first Day of August, 2004

JON W. DUDAS
*Director of the United States Patent and Trademark Office*